(12) United States Patent
Bono et al.

(10) Patent No.: US 7,306,602 B2
(45) Date of Patent: Dec. 11, 2007

(54) SNAP-IN WASHERS AND ASSEMBLIES THEREOF

(75) Inventors: Frank Bono, Rehoboth, MA (US);
Amie Borgstrom, North Attleborough, MA (US); William Dunbar, Jr., Norton, MA (US); Chris Fair, Denver, CO (US); Ronald L. Sacher, Needham, MA (US)

(73) Assignee: Depuy Actomed, Inc., Raynham, MA (US)

( * ) Notice: Subject to any disclaimer, the term of this patent is extended or adjusted under 35 U.S.C. 154(b) by 0 days.

(21) Appl. No.: 10/285,055

(22) Filed: Oct. 31, 2002

(65) Prior Publication Data

US 2004/0087949 A1    May 6, 2004

(51) Int. Cl.
*A61B 17/56* (2006.01)
*A61B 17/58* (2006.01)

(52) U.S. Cl. .................................................. 606/61
(58) Field of Classification Search ............. 606/61, 606/69, 70, 71, 72, 73, 60
See application file for complete search history.

(56) References Cited

U.S. PATENT DOCUMENTS

| | | | |
|---|---|---|---|
| 680,560 A | 8/1901 | Barnes | |
| 2,004,182 A | 6/1935 | Arey | |
| 4,341,382 A | 7/1982 | Arnold | |
| 4,771,767 A | 9/1988 | Steffee | |
| 4,778,321 A | 10/1988 | Okawa | |
| 4,836,196 A * | 6/1989 | Park et al. ............. | 606/61 |
| 4,896,571 A | 1/1990 | Perry | |
| 5,084,048 A * | 1/1992 | Jacob et al. ............ | 606/61 |
| 5,129,899 A | 7/1992 | Small et al. | |
| 5,190,543 A | 3/1993 | Schlapfer | |
| 5,269,784 A * | 12/1993 | Mast ...................... | 606/69 |
| 5,304,179 A | 4/1994 | Wagner | |
| 5,312,404 A * | 5/1994 | Asher et al. ............ | 606/61 |
| 5,344,422 A | 9/1994 | Frigg | |
| 5,352,226 A | 10/1994 | Lin | |
| 5,380,323 A | 1/1995 | Howland | |
| 5,395,371 A | 3/1995 | Miller et al. | |
| 5,429,639 A | 7/1995 | Judet | |
| 5,474,551 A | 12/1995 | Finn | |
| 5,487,744 A | 1/1996 | Howland | |
| 5,501,684 A | 3/1996 | Schlapfer et al. | |
| 5,531,745 A * | 7/1996 | Ray ........................ | 606/61 |
| 5,562,661 A | 10/1996 | Yoshimi et al. | |
| 5,609,592 A | 3/1997 | Brumfield et al. | |
| 5,613,968 A | 3/1997 | Lin | |
| 5,743,907 A | 4/1998 | Asher et al. | |
| 5,776,134 A | 7/1998 | Howland | |
| 5,810,818 A | 9/1998 | Errico | |

(Continued)

FOREIGN PATENT DOCUMENTS

EP    0 947 174 A    10/1999

(Continued)

*Primary Examiner*—Pedro Philogene

(57) ABSTRACT

This invention relates to an apparatus for spinal fixation, in particular, for joining a bone anchor with spinal stabilizers such as a spinal rod or spinal plate in a polyaxial fashion. The invention is also directed to polyaxial connectors which incorporate arcuate washers. The polyaxial features of this invention are achieved preferably with snap-in washers which minimize the numbers of parts that a surgeon may have to handle during surgery.

4 Claims, 6 Drawing Sheets

U.S. PATENT DOCUMENTS

| | | |
|---|---|---|
| 5,814,046 A | 9/1998 | Hopf |
| 5,879,351 A | 3/1999 | Viart |
| 5,879,851 A | 3/1999 | Takahashi |
| 5,938,663 A | 8/1999 | Petreto |
| 5,976,135 A * | 11/1999 | Sherman et al. .............. 606/61 |
| 5,980,521 A | 11/1999 | Montague et al. |
| 5,984,924 A * | 11/1999 | Asher et al. .................. 606/61 |
| 6,030,388 A | 2/2000 | Yoshimi et al. |
| 6,042,582 A | 3/2000 | Ray |
| 6,050,997 A | 4/2000 | Mullane |
| 6,080,156 A * | 6/2000 | Asher et al. .................. 606/61 |
| 6,083,226 A | 7/2000 | Fiz |
| 6,110,172 A * | 8/2000 | Jackson ....................... 606/61 |
| 6,123,706 A * | 9/2000 | Lange .......................... 606/61 |
| 6,146,383 A | 11/2000 | Studer et al. |
| 6,179,838 B1 * | 1/2001 | Fiz ............................... 606/61 |
| 6,183,473 B1 | 2/2001 | Ashman |
| 6,187,005 B1 | 2/2001 | Brace et al. |
| 6,231,575 B1 | 5/2001 | Krag |
| 6,254,603 B1 | 7/2001 | Gertzbein et al. |
| 6,273,914 B1 * | 8/2001 | Papas ..................... 623/17.11 |
| 6,280,443 B1 | 8/2001 | Gu et al. |
| 6,280,445 B1 * | 8/2001 | Morrison et al. ............. 606/61 |
| 6,287,309 B1 * | 9/2001 | Baccelli et al. ............... 606/61 |
| 6,299,614 B1 | 10/2001 | Kretschmer et al. |
| 6,315,779 B1 | 11/2001 | Morrison et al. |
| 6,641,583 B2 * | 11/2003 | Shluzas et al. ............... 606/61 |
| 6,673,074 B2 | 1/2004 | Shluzas |
| 2002/0026194 A1 | 2/2002 | Morrison et al. |
| 2002/0029040 A1 | 3/2002 | Morrison et al. |
| 2002/0035367 A1 | 3/2002 | Ritland |
| 2002/0049446 A1 | 4/2002 | Harkey, III et al. |
| 2002/0143328 A1 * | 10/2002 | Shluzas et al. ............... 606/61 |
| 2003/0028191 A1 | 2/2003 | Shluzas et al. |
| 2004/0019353 A1 * | 1/2004 | Freid et al. ................... 606/69 |
| 2004/0092939 A1 | 5/2004 | Freid et al. |

FOREIGN PATENT DOCUMENTS

| | | | |
|---|---|---|---|
| EP | 1 180 348 A2 | 2/2002 | |
| FR | 2 743 290 A | 7/1997 | |
| FR | 2743290 * | 7/1997 | ............... 606/61 |
| FR | 2 743 290 | 11/1997 | |
| FR | 2815535 A1 | 4/2002 | |
| WO | WO 00/54681 * | 9/2000 | ............... 606/61 |
| WO | WO 00/54681 A | 9/2000 | |

* cited by examiner

SNAP-IN WASHERS AND ASSEMBLIES THEREOF

BACKGROUND OF THE INVENTION

1. Field of the Invention

This invention relates to connecting devices for spinal fixation, in particular, for joining a bone anchor with spinal stabilizers such as a spinal rod or spinal plate in a polyaxial fashion.

2. Related Art

It is well know and practiced that when securing and maintaining bones in a preferred alignment, a plurality of bone anchors may be attached to one or more bones and subsequently secured together in a desired orientation with a bone stabilizer. Examples of bone stabilizers include "longitudinal members," and in some cases, "connectors" as is known in the art. That is, the longitudinal member (e.g. a rod or a plate) connects the bone anchors together, and (if needed), the connectors are used to secure the bone anchor to the longitudinal member. Accordingly, there are at least two criteria that would be desirable to be satisfied when securing bones in a desired alignment using bone anchors and a bone stabilizer:

(i) it is desirable to attach each bone anchor to a bone in a manner that will inhibit movement of the anchor relative to the bone. Thus, the orientation of the bone anchor to its attached bone may be dependent on, e.g., the bone configuration, density, and/or fractures therein;

(ii) the bone stabilizer must be attached to each bone anchor, and in particular, to an included shaft, in a manner so that the longitudinal member (of the bone stabilizer) is oriented to effectively maintain the desired alignment of bones.

In order to satisfy the above criteria, it may be preferable that the shafts of the bone anchors are not parallel to each other and/or not perpendicular to the longitudinal member when they are attached to their respective bones. Moreover, for each bone alignment procedure performed using bone anchors and bone stabilizers, the orientations of the shafts relative to one another and the longitudinal member may be substantially unique.

Accordingly, a preferable position of the longitudinal member can be compromised by the various orientations of the bone anchoring shafts, these various orientations due to, e.g., the preferred positions of the anchors when they are secured to the bones. Thus, it is advantageous to have the ability to firmly secure such bone anchoring shafts to a bone position retainer, wherein the shafts may be at various orientations to the longitudinal member, i.e., in polyaxial or multi-angular orientations.

U.S. Pat. No. 5,984,924 discloses such a bone alignment system capable of multi-angular orientations with respect to the bone anchor and longitudinal member. Through use of a system of concave or convex arcuate washers, the multi-angular orientations are achieved.

U.S. Pat. No. 6,315,779 discloses a multi-axial bone fixation implant having an elongated member, one or more bone anchor assemblies, and stabilizer members which are fitted within the elongated member. The stabilizer members are rectilinear in shape and do not include arcuate surfaces. The only use of washers disclosed are ones having an undercut within its oblong aperture on the top of the implant. The implant is locked by a nut and the washer atop the elongated member, the enlarged portion of a bone anchor is forced against an inside wall of the stabilizer, which is in turn locks against the elongated member. Disadvantages of this system are the large number of separate parts and that the washers can be cumbersome to use in that they are not secured to the elongated member.

The present invention provides an advance in the art by minimizing a number of parts a surgeon has to handle during a surgical procedure while having the advantage of multiple orientations provided by use of the arcuate washers.

BRIEF DESCRIPTION OF THE DRAWINGS

The invention will be more fully understood from the following detailed description taken in conjunction with the accompanying drawings, in which.

SUMMARY OF THE INVENTION

One embodiment of the invention is directed toward a connecting device for joining a spinal stabilizer with a bone anchor comprising:

a body comprising a bone anchor fastening portion and a spinal stabilizer fastening portion, wherein the bone anchor fastening portion comprises an aperture for receiving and retaining a washer.

Another embodiment of the invention is directed toward a connecting device for joining a spinal stabilizer with a bone anchor comprising:

a body comprising a clamp with two projecting arm portions, the clamp portion for fastening a spinal stabilizer in the form of a rod and the arm portions having apertures for fastening the bone anchor.

Another embodiment of the invention relates to a connecting device for joining two bone anchors comprising a plate having an aperture for receiving and retaining a washer.

Yet another embodiment of the invention comprises a washer comprising a concave or convex arcuate portion and a fastening portion, wherein the fastening portion comprises flexible projections for receipt and retention in a channel.

Another embodiment of this invention relates to a systems for spinal stabilization comprising a spinal rod; a bone anchor comprising a bone engaging first portion, a machine threaded second portion for engaging a locking nut, and a third portion, intermediate to the first and second portions, comprising arcuate surfaces for polyaxial engagement with a connector; and a locking nut; wherein, the bone anchor and rod are joined by the connecting devices as hereinafter described and claimed. Additionally, systems of this invention may comprise at least two bone anchors as described above joined by a plate having an aperture for receiving and retaining a washer.

DETAILED DESCRIPTION OF PREFERRED EMBODIMENTS OF THE INVENTION

Generally, this invention deals with devices for spinal fixation especially to those used particularly for joining a bone anchor with spinal stabilizers such as a spinal rod or spinal plate in a polyaxial fashion. The invention is also directed to polyaxial connectors which incorporate arcuate washers. The polyaxial features of this invention are achieved preferably with snap-in washers which minimize the numbers of parts that a surgeon may have to handle during surgery.

Figure 1:
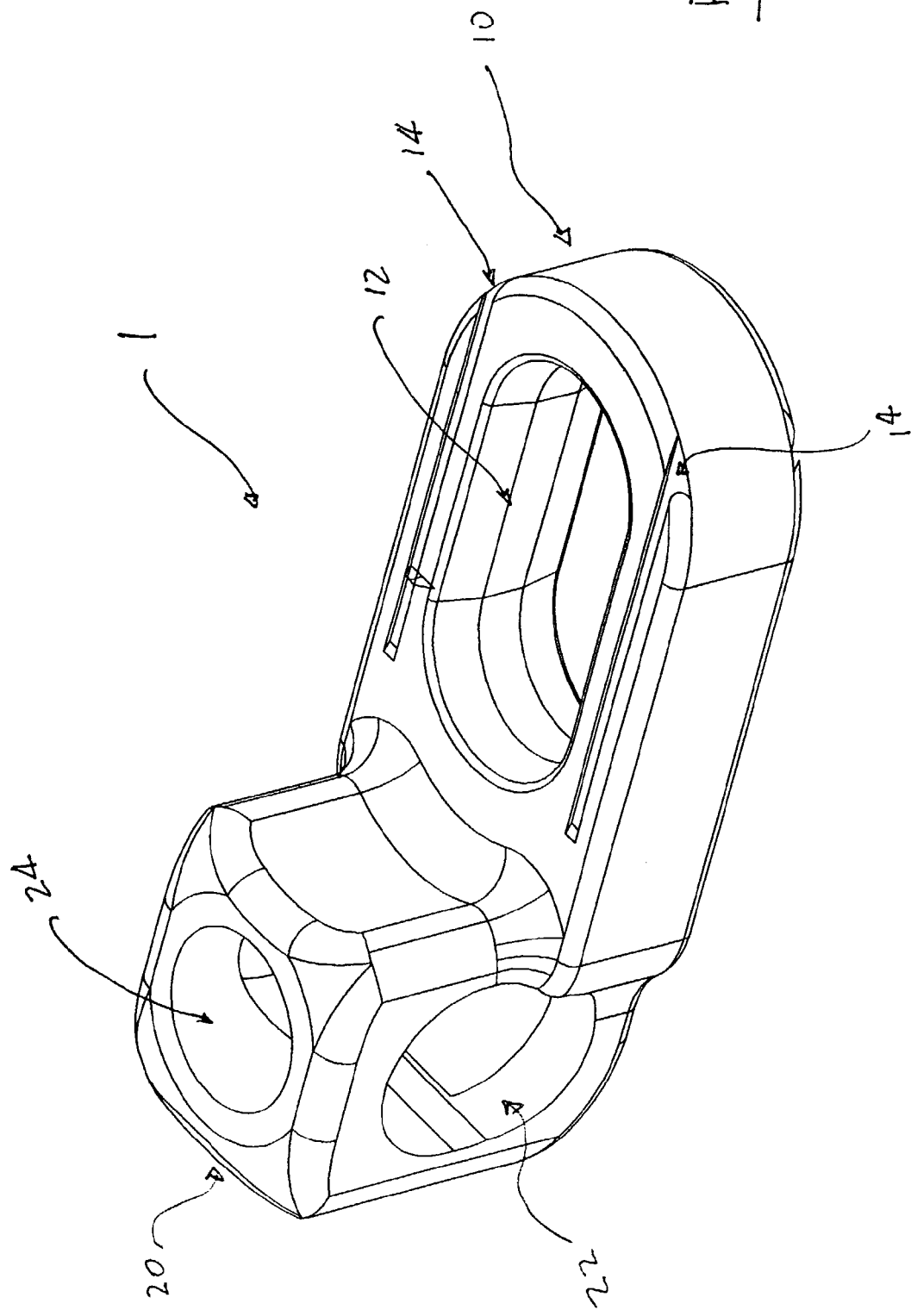
FIG. 1 depicts a bone anchor-spinal stabilizer connector of this invention.
Figure 4:
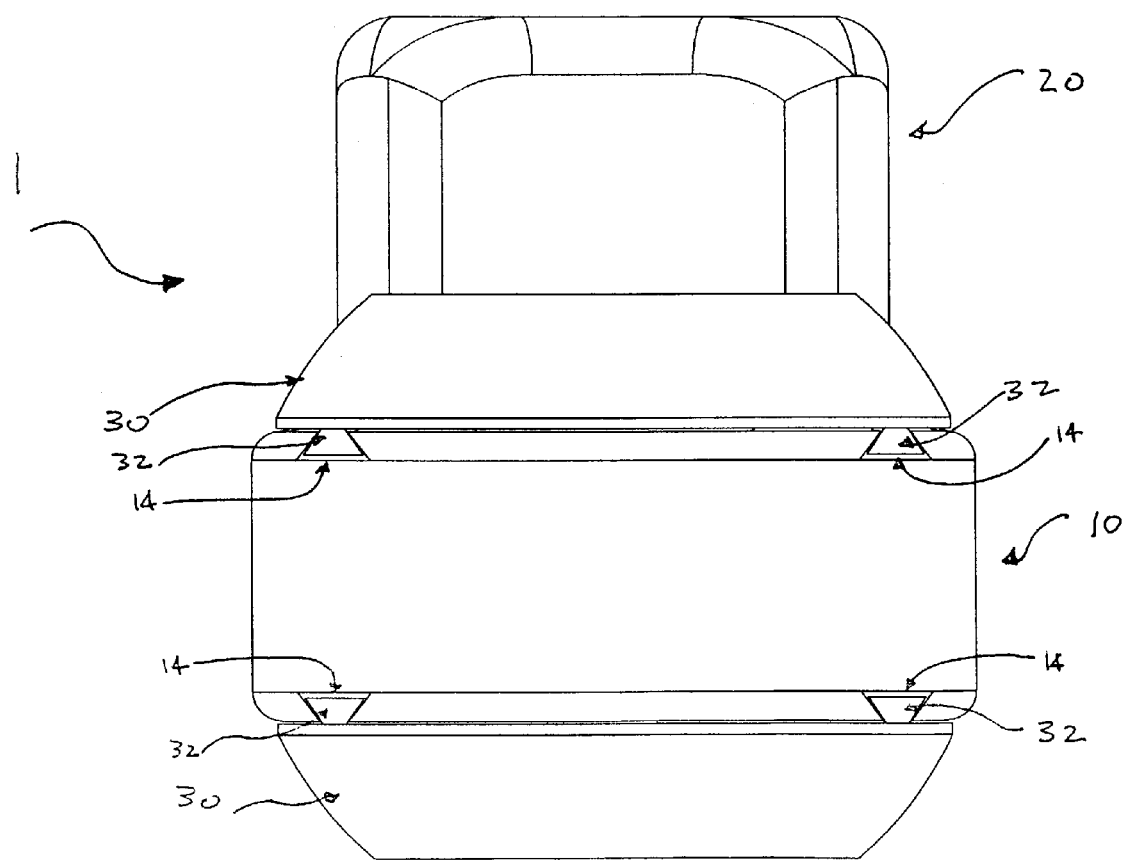
FIG. 4 depicts a cross-sectional side view of bone anchor-spinal stabilizer connector of this invention incorporating top and bottom washers.

FIG. 1 depicts spinal stabilizer-bone anchor connector 1. Connector 1 comprises spinal stabilizer portion 20 and bone anchor portion 10. Spinal stabilizer portion 20 comprises a stabilizer receiving throughbore 22 and a set screw bore 24. Thus in attaching to a stabilizer, a stabilizer (rod) will pass through bore 22 and be secured into place by the locking of a set screw through bore 22 by securely contacting the stabilizer. Portion 10 of the device includes aperture 12 for receiving a head of a bone anchor and channels 14 for receipt of washers. The bone anchors contemplated for use of this invention are those well known in the art which generally comprise a bone engaging threaded first portion, a machine threaded second portion for engaging a locking nut, and a third portion, intermediate to the first and second portions, comprising arcuate surfaces for polyaxial engagement with the connector, for example, as depicted in FIG. 4 of U.S. Pat. No. 5,984,924 or in FIG. 7 of U.S. Pat. No. 6,315,779, the disclosures of which are incorporated by reference in their entirety.

Figure 2:
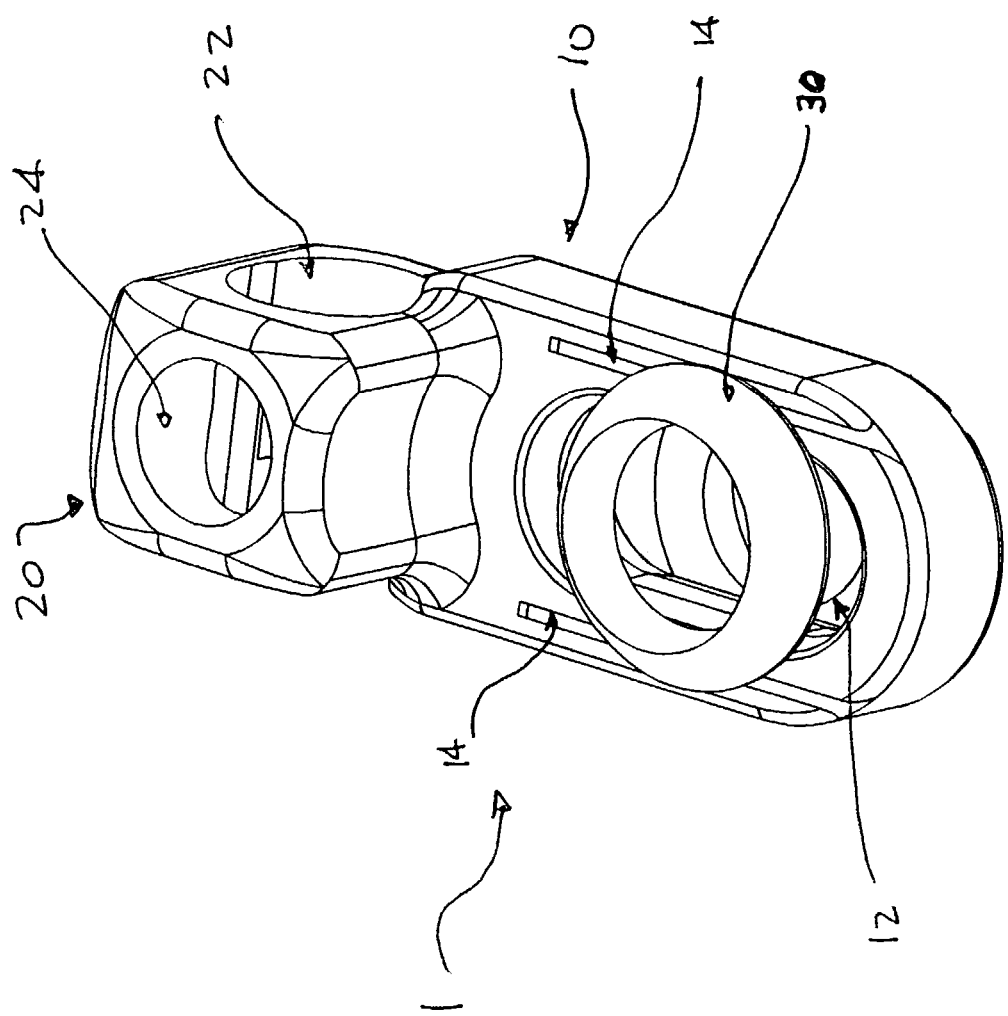
FIG. 2 depicts another view of the bone anchor-spinal stabilizer connector of FIG. 1 incorporating a washer.

FIG. 2 depicts the connector 1 incorporating washer 30.

Figure 3:
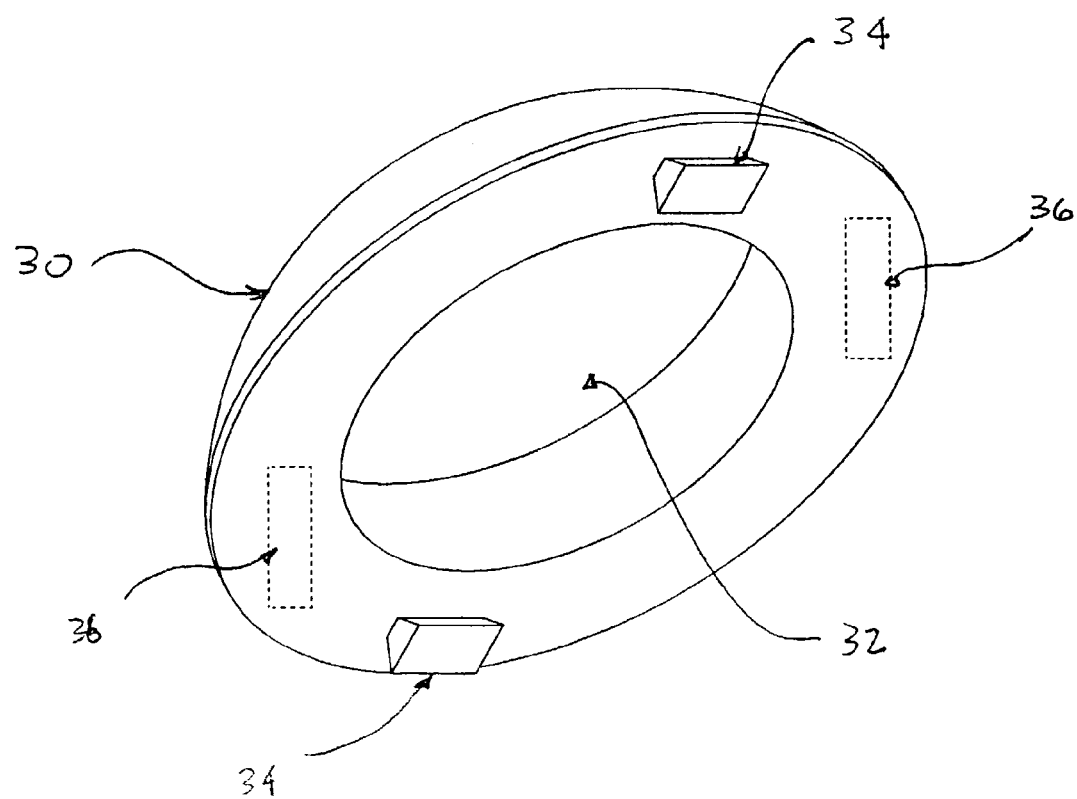
FIG. 3 depicts one embodiment for the washers of this invention.

FIG. 3 depicts washer 30 comprising aperture 32 for receiving the head of a bone anchor. Projections 34 are sized to engage channels 14. Optionally spacers 36 (shown in phantom) may be employed to provide spacing between the body of the washer and portion 10 of connector 1.

FIG. 4 is a cross-sectional depiction of connector 1. Portion 10 comprises channels 14 which receive projection 32 of washers 30. Preferably projections 32 of washers 30 are biased to securely fit in channels 14.

Figure 5:
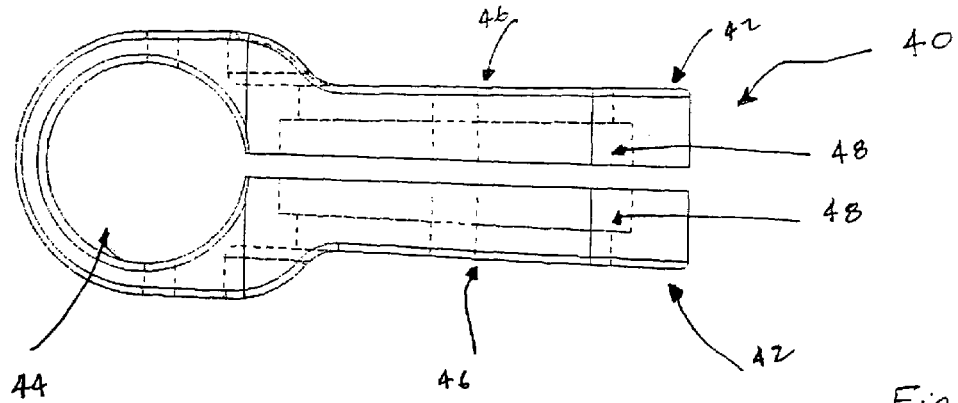
FIG. 5 depicts a cross-sectional view of the band-clamp embodiment of this invention.

FIG. 5 depicts the band clamp 40 embodiment of this invention. Clamp 40 comprises two projecting arm portions 42 with aperture 44 for engaging a spinal stabilizer in the form of a rod and arm portions 42 having apertures 46 for fastening to a bone anchor. Each arm portion 42 comprises channels 48 for receiving projections of washers (not shown).

Figure 6:
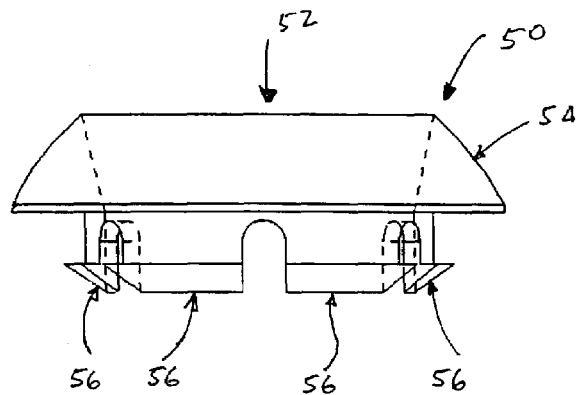
FIG. 6 depicts a resilient snap-in washer embodiment of this invention.

FIG. 6 depicts washer 50 suitable for use with band clamp 40. Washer 50 comprises throughbore 52, concave surface 54 and projects 56 which engage channels 48 (not shown) of band clamp 40.

Figure 7:
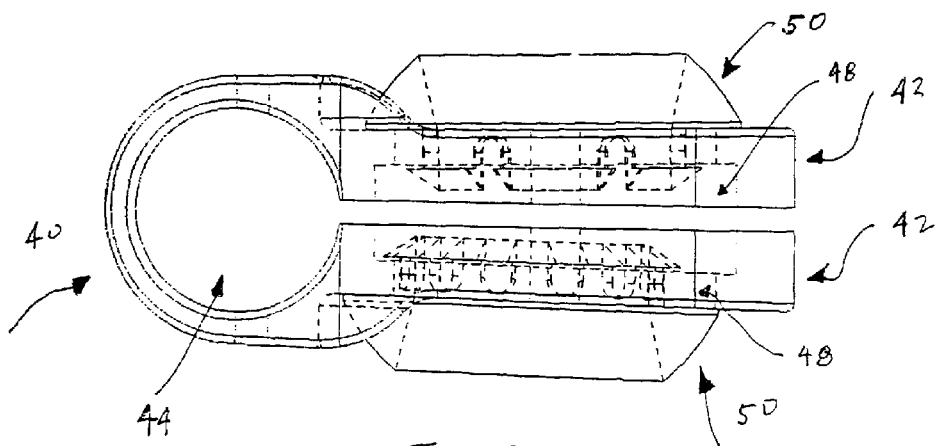
FIG. 7 depicts a cross-sectional view of the band-clamp embodiment of this invention incorporating the resilient snap-in washers.

FIG. 7 depicts the assembled clamp 40 with washers 50 engaged in channels 48.

Figure 8:
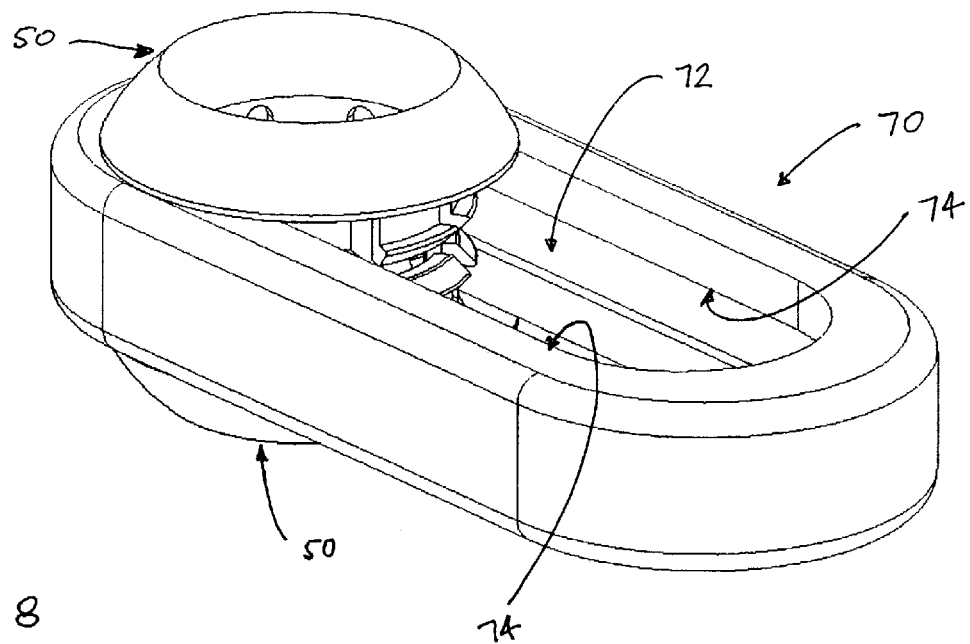
FIG. 8 depicts a perspective view of a bone plate embodiment of this invention incorporating the resilient snap-in washers.

FIG. 8 depicts the bone plate 70 embodiment of this invention. Plate 70 comprises aperture 72 for receiving and retaining washers 50 in channels 74. In this figure, both top and bottom washers are depicted. Engagement of washers 50 into channels 74 are as described for the band clamp embodiment of this invention. Furthermore, bone plate 70 would actually have at least two additional washers (one top and one bottom) for a total of 4 resilient washers so that connection between at least 2 bone anchors may be made.

Figure 9:
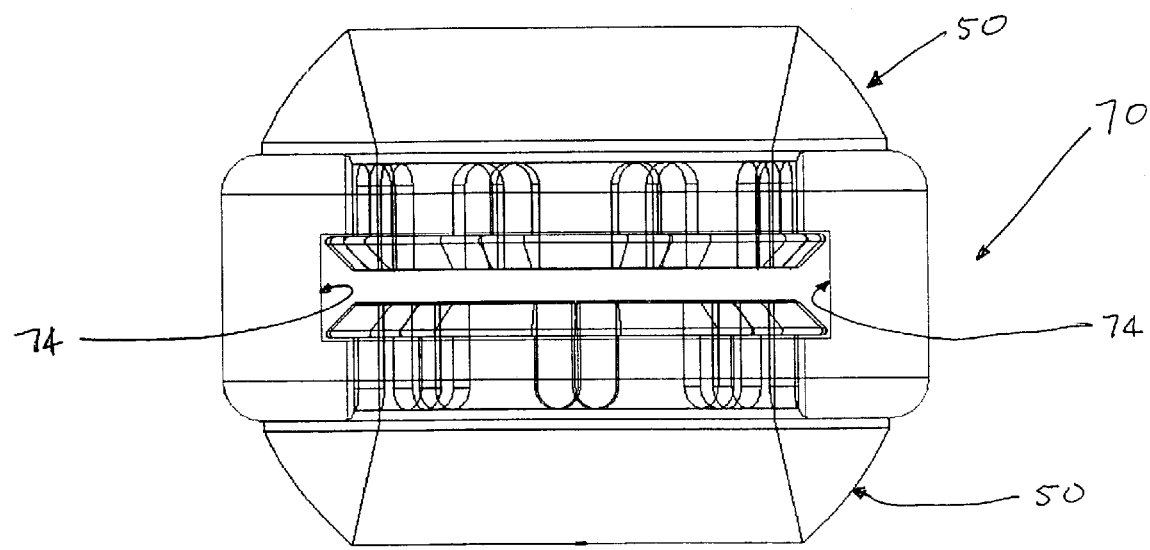
FIG. 9 depicts a cross-sectional end view of the bone plate of FIG. 8.

FIG. 9 depicts a cross-sectional end view of bone plate 70 shown in FIG. 8. Referring to FIG. 9, channels 74 for receiving washers 50 are more clearly seen.

Although washers 30 and 50 of this invention have been depicted with concave surfaces, it is apparent to one skilled in the art that washers having other arcuate surfaces, such as convex surfaces, may also be used depending on the nature of engagement with the corresponding bone anchor and locking nut such as through well know bone anchors as depicted, for example, in U.S. Pat. No. 5,984,924 or in U.S. Pat. No. 6,315,779.

Also the invention relates to systems for spinal stabilization comprising a spinal rod; a bone anchor comprising a bone engaging first portion, a machine threaded second portion for engaging a locking nut, and a third portion, intermediate to the first and second portions, comprising arcuate surfaces for polyaxial engagement with a connector; and a locking nut used in combination with the connecting devices of this invention as described above. Additional systems of this invention include a system for spinal stabilization comprising at least two bone anchors comprising a bone engaging first portion, a machine threaded second portion for engaging a locking nut, and a third portion, intermediate to the first and second portions, comprising arcuate surfaces for polyaxial engagement with a connector; and a locking nut, wherein, the bone anchors are joined by the connecting device comprising a plate having an aperture for receiving and retaining a washer.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A connecting device comprising:
   a body including an oblong aperture for receiving a portion of a bone anchor and an opening for receiving a spinal rod,
   a first washer received and retained by the body, the first washer positioned on the top surface of the body and having an opening aligned with the oblong aperture, the first washer being rotatable about an axis that intersects the opening and the oblong aperture; and
   a second washer received and retained by the body, the second washer positioned on the bottom surface of the body and having an opening aligned with the oblong aperture, the first washer being rotatable relative to the second washer.

2. The connecting device of claim 1, wherein the second washer is rotatable about an axis that intersects the opening of the second washer and the oblong aperture.

3. The connecting device of claim 1, wherein the first washer and the second washer are independently rotatable.

4. A connecting device comprising:
   a body including an oblong aperture for receiving a portion of a bone anchor and an opening for receiving a spinal rod,
   a first washer received and retained by the body, the first washer positioned on the top surface of the body and having an opening aligned with the oblong aperture, the first washer being rotatable about an axis that intersects the opening and the oblong aperture; and
   a second washer received and retained by the body, the second washer positioned on the bottom surface of the body and having an opening aligned with the oblong aperture, the first washer being rotatable relative to the second washer, the first washer and the second washer rotatable relative to the bone anchor.

* * * * *